United States Patent [19]

Balow et al.

[11] Patent Number: 6,093,807
[45] Date of Patent: Jul. 25, 2000

[54] SUGAR-MODIFIED 7-DEAZA-7-SUBSTITUTED OLIGONUCLEOTIDES

[75] Inventors: Guity P. Balow, Vista; Oscar L. Acevedo, San Diego; Phillip Dan Cook, Fallbrook, all of Calif.

[73] Assignee: Isis Pharmaceuticals, Inc., Carlsbad, Calif.

[21] Appl. No.: 09/272,977

[22] Filed: Mar. 19, 1999

Related U.S. Application Data

[60] Provisional application No. 60/078,637, Mar. 19, 1998.

[51] Int. Cl.$^7$ .................................................. C07H 21/02
[52] U.S. Cl. ................... 536/23.1; 536/27.2; 536/27.13; 536/27.6; 536/27.62; 536/27.63; 536/27.7
[58] Field of Search ................................ 536/23.1, 27.13, 536/27.2, 27.6, 27.62, 27.63, 27.7

[56] References Cited

U.S. PATENT DOCUMENTS

| 5,210,264 | 5/1993 | Yau ........................................ 558/167 |
| 5,594,121 | 1/1997 | Froehler et al. ....................... 536/23.5 |
| 5,898,031 | 4/1999 | Crooke ................................. 435/172.3 |

FOREIGN PATENT DOCUMENTS

| 14398/88 | 10/1988 | Australia . |
| 0 626 387 B1 | 3/1999 | European Pat. Off. . |
| WO 93/09127 | 5/1993 | WIPO . |

OTHER PUBLICATIONS

Agrawal, S. (ed.), *Protocols for Oligonucleotides and Analogs*, Humana Press, Totowa, NJ, 1993.

Buhr et al., "Oligodeoxynucleotides containing C–7 propyne analogs of 7–deaza–2'–deoxyguanosine and 7–deaza–2'–deoxyadenosine," *Nucl. Acids Res.*, 1996, 24(15), 2974–2980.

Englisch, U. et al., "Chemically Modified Oligonucleotides as Probes and Inhibitors", *Angew. Chem. Int. Ed. Eng.*, 1991, 30, 613–629.

Freier, S.M. et al., "The ups and downs of nucleic acid duplex stability: structure–stability studies on chemically–modified DNA:RNA duplexes", *Nucl. Acids Res.*, 1997, 25, 4429–4443.

Kroschwitz, J.I., "Polynucleotides", *Concise Encyclopedia of Polymer Science and Engineering*, 1990, John Wiley & Sons, New York, 858–859.

Ludwig, J. et al., "Rapid and Efficient Synthesis of Nucleoside 5'–O–(1–Thiotriphosphates), 5'–Triphosphates and 2',3'–Cyclophosphorothioates Using 2'Chloro–4H–1,3,2–benzodioxaphosphorin–4–one", *J. Org. Chem.*, 1989, 54, 631–635.

Martin, P., "Ein neuer Zugang zu 2'–O–Alkylribonucleosiden und Eigenschaften deren Oligonucleotide", *Helvetica Chemica Acta*, 1995, 78, 486–504.

Seela et al., "Duplex Stabilization of DNA: Oligonucleotides Containing 7–Substituted 7–Deazaadenines," *Helv. Chim. Acta*, 1995, 78, 94–108.

Seela et al., "Oligonucleotide Duplex Stability Controlled by the 7–Substituents of 7–Deazaguanine Bases," *Bioorg. Med. Chem. Lett.*, 1995, 5(24), 3059–3052.

Tu et al., "3'–End labeling of DNA with [α–$^{32}$P] cordycepin–5'–triphosphate," *Gene*, 1980, 10, 177–183.

*Primary Examiner*—James O. Wilson
*Attorney, Agent, or Firm*—Woodcock Washburn Kurtz Mackiewicz & Norris LLP

[57] ABSTRACT

Functionalized nucleomonomers and oligonucleotides are provided which have increased nuclease resistance and enhanced binding affinity to target DNA or RNA molecules. The oligonucleotides of the present invention comprise at least one 7-deaza-7-iodo-2'-substituted purine, herein referred to as a functionalized nucleomonomer. A preferred 2' substituent on the sugar moiety is a 2'-O-alkoxy alkyl group. More preferably, the 2'-substituent is 2'—O—CH$_2$—CH$_2$—O—CH$_3$ (or 2'-methoxyethoxy). Such oligonucleotides are useful as therapeutics for modulating protein expression in organisms and treating disease states susceptible to oligonucleotide therapeutics. Such oligonucleotides are also useful as diagnostics for the diagnosis and detection of disease states, and as research reagents.

11 Claims, No Drawings

SUGAR-MODIFIED 7-DEAZA-7-SUBSTITUTED OLIGONUCLEOTIDES

This application claims benefit to U.S. provisional application Ser. No. 60/078,637 filed Mar. 19, 1998.

FIELD OF THE INVENTION

This invention is directed to functionalized nucleotides, nucleosides and oligonucleotides bearing chemically modified bases and sugar moieties. Included in the invention are oligonucleotides wherein at least one of the nucleotide units of the oligonucleotide bears a modified base and a modified sugar moiety to increase resistance of the oligonucleotide against degradation by nucleases and to increase binding affinity of the oligonucleotide to a complementary strand of nucleic acid. The functionalized nucleotides and nucleosides of the invention include a 7-deaza-7-substituted purine connected to a 2'-O-methoxyethyl-β-D-ribofuranosyl sugar moiety.

BACKGROUND OF THE INVENTION

It is well known that most of the bodily states in mammals, including most disease states, are affected by proteins. Classical therapeutic modes have generally focussed on interactions with such proteins in an effort to moderate their disease-causing or disease-potentiating functions. However, recently, attempts have been made to moderate the actual production of such proteins by interactions with molecules that direct their synthesis, such as intracellular RNA. By interfering with the production of proteins, maximum therapeutic effect and minimal side effects may be realized. It is the general object of such therapeutic approaches to interfere with or otherwise modulate gene expression leading to undesired protein formation.

One method for inhibiting specific gene expression is the use of oligonucleotides. Oligonucleotides are now accepted as therapeutic agents with great promise. Oligonucleotides are known to hybridize to single-stranded DNA or RNA molecules. Hybridization is the sequence-specific base pair hydrogen bonding of nucleobases of the oligonucleotide to the nucleobases of the target DNA or RNA molecule. Such nucleobase pairs are said to be complementary to one another.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

For use as therapeutics, oligonucleotides must be transported across cell membranes or be taken up by cells, and appropriately hybridize to target DNA or RNA. These critical functions depend on the initial stability of the oligonucleotides toward nuclease degradation. A serious deficiency of unmodified oligonucleotides which affects their hybridization potential with target DNA or RNA for therapeutic purposes is the enzymatic degradation of administered oligonucleotides by a variety of intracellular and extracellular ubiquitous nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and resist nuclease degradation. Several publications describe the synthesis of 7-deaza-7-substituted-2'-deoxypurine nucleosides and their incorporation into oligonucleotides. Buhr et al., *Nucleic Acids Research*, 1996, 24, 2974; Seela and Thomas, *Helv. Chim. Acta*, 1995, 78, 94; Seela et al., *Bioorg. Med. Chem. Lett.*, 1995, 5, 3059.

Other publications describe 7-deaza-7-substituted-2'-substituted purines, wherein the 7-substituent is bromo, chloro, cyano, alkyl, alkynyl, aryl or heteroaryl, and the 2'-substituent includes hydroxyl, alkoxyl or alkoxyalkoxyl.

International Publication Number WO 93/09127, published May 13, 1993, describes 7-deaza-7-substituted-2'-substituted purines wherein the 7-substituent is bromo, chloro, fluoro, cyano, alkyl or alkynyl, and the 2'-substituent is hydrogen, or a hydroxyl or alkoxy group.

U.S. Pat. No. 5,594,121, issued Jan. 14, 1997, discloses 7-deaza-7-substituted-2'-substituted purines wherein the 7-substituent is an aryl, heteroaryl or alkynylheteroaryl group, and the 2'-substituent is hydrogen, or a hydroxyl, fluoro or alkoxyl group.

European Patent Application Number 94810255.3, filed May 3, 1994, describes 7-deaza-7-substituted-2'-substituted purines wherein the 7-substituent is cyano or an alkynyl group, and the 2'-substituent includes a methoxyethoxy group.

Australian Patent Application AU-A-14398/88, published Oct. 13, 1988, describes 7-deaza-7-substituted-2'-substituted purines wherein the 7-substituent is halo, hydroxyl, mercapto, alkyl or alkylthio, and the 2'-substituent is hydrogen or hydroxyl.

While it has been recognized that nucleosides and oligonucleotides bearing base and sugar modifications would be useful, there remains a long-felt need for oligonucleotides with greater binding affinity, hence improved hybridization characteristics, and greater nuclease resistance. Such oligonucleotides are desired as therapeutics, diagnostics, and research reagents.

SUMMARY OF THE INVENTION

The present invention provides functionalized nucleomonomers comprising 7-deaza-7-substituted purines bearing 2'-O-substituted-β-D-ribofuranosyl sugar moieties. The functionalized nucleomonomers of the invention are incorporated into oligomeric compounds that include analogs of native nucleic acids, chimeric compounds comprising heterogenous linkages, and oligonucleosides.

The functionalized nucleomonomers of the present invention have the formula:

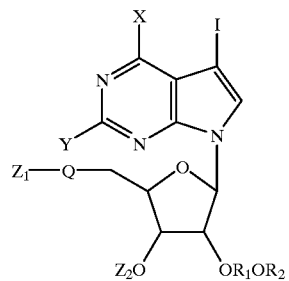

wherein:

X is Cl, OH, SH, $SR_3$, $OR_1$, CN or N(H)J;

Y is OH, SH, $SR_3$, $OR_3$, CN or N(H)J;

each J is, independently, hydrogen or an amino protecting group;

Q is O or $CH_2$;

$Z_1$ is H, a group useful in oligonucleotide synthesis or a phosphite moiety;

$Z_2$ is H, a phosphate moiety, or a group useful in oligonucleotide synthesis;

each $R_1$, $R_2$ and $R_3$ is, independently, $C_1$–$C_{10}$ alkyl;

each $R_4$ and $R_5$ is, independently, straight or branched chain $C_1$–$C_{10}$ alkyl, or $R_4$ and $R_5$ together are —$(CH_2)_n$— or —$(CH_2)_n$—O—$(CH_2)_n$;

each $R_6$ is, independently, H, $C_1$–$C_{10}$ alkyl, aryl or haloaryl;

$R_7$ is selected from a group consisting of H, $C_1$–$C_{10}$ alkyl, aryl and haloaryl;

$R_8$ is haloaryl; and n is 2 to 7.

In accordance with one embodiment of the present invention there are provided functionalized nucleomonomers which are chemically modified to increase the nuclease resistance and improve hybridization characteristics or binding affinity of oligomeric compounds containing the nucleomonomers to target DNA or RNA. The heterocyclic base of the functionalized nucleomonomers of the present invention is a 7-deaza-7-iodo purine moiety that includes 7-deaza-7-iodo adenine and 7-deaza-7-iodo guanine. The sugar moiety of the functionalized nucleomonomers of the present invention is functionalized with a 2'-O-alkoxy alkyl substituent to increase the nuclease resistance of oligomeric compounds that incorporate these functionalized nucleomonomers. A preferred 2'-O-alkoxy alkyl substituent is a 2'-O-methoxyethyl group.

The present invention further provides oligonucleotides formed from a sequence of nucleomonomers wherein at least one of the nucleomonomers is a functionalized nucleomonomer of the invention comprising a 7-deaza-7-iodo-2'-substituted purine. In a preferred embodiment, the 2'-substituent is 2'-O-alkoxy alkyl. In a further preferred embodiment, the 2'-O-alkoxy alkyl substituent is 2'-methoxyethoxy.

The oligomeric compounds of the present invention include a plurality of nucleomonomers, at least one of said nucleomonomers being a functionalized nucleomonomer of the present invention. In one embodiment of the invention nucleomonomers and functionalized nucleomonomers are joined via internucleoside linkages and substitute internucleoside linkages. In a preferred embodiment of the present invention the internucleoside linkage connecting nucleomonomers and functionalized nucleomonomers are charged phosphorus linkages selected from a group consisting of phosphodiester and phosphorothioate linkages.

DETAILED DESCRIPTION OF THE INVENTION

In accordance with the present invention, novel monomeric and oligomeric compounds are provided. The novel monomeric compounds are nucleosides and nucleotides having a 7-deaza-7-(cyano or iodo) heterocyclic base, that may be further substituted, attached to a 2'-O-alkoxyalkyl ribosyl sugar moiety. The novel monomeric compounds are referred to herein as "functionalized nucleomonomers". Oligomeric compounds of the invention comprise at least one functionalized nucleomonomer and naturally occurring or synthetic nucleotides and nucleosides (nucleomonomers) joined via linking groups. The oligomeric compounds of the invention have increased nuclease resistance and improved binding affinity to complementary strands of target nucleic acids.

The functionalized nucleomonomers of the present invention have the formula:

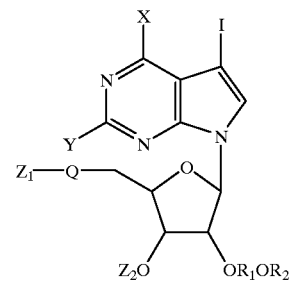

wherein:

X is Cl, OH, SH, $SR_3$, $OR_1$, CN or N(H)J;

Y is OH, SH, $SR_3$, $OR_3$, CN or N(H)J;

each J is, independently, hydrogen or an amino protecting group;

Q is O or $CH_2$;

$Z_1$ is H, a group useful in oligonucleotide synthesis or a phosphite moiety;

$Z_2$ is H, a phosphate moiety, or a group useful in oligonucleotide synthesis;

each $R_1$, $R_2$ and $R_3$ is, independently, $C_1$–$C_{10}$ alkyl;

each $R_4$ and $R_5$ is, independently, straight or branched chain $C_1$–$C_{10}$ alkyl, or $R_4$ and $R_5$ together are —$(CH_2)_n$— or —$(CH_2)_n$—O—$(CH_2)_n$;

each $R_6$ is, independently, H, $C_1$–$C_{10}$ alkyl, aryl or haloaryl;

$R_7$ is selected from a group consisting of H, $C_1$–$C_{10}$ alkyl, aryl and haloaryl;

$R_8$ is haloaryl; and n is 2 to 7.

In a preferred embodiment of the present invention oligomeric compounds comprise nucleomonomers and at least one functionalized nucleomonomer joined together by phosphorus linkages such as phosphodiester and phosphorothioate linkages.

A preferred list of heterocyclic base moieties that are routinely utilized in the preparation of nucleomonomers amenable to the present invention include purines and pyrimidines such as adenine, guanine, cytosine, uridine and thymine, as well as other synthetic and natural bases such as xanthine, hypoxanthine, 2-aminoadenine, 6-methyl and other alkyl derivatives of adenine and guanine, 2-propyl and other derivatives of adenine and guanine, 5-halouracil and cytosine, 5-propynyl uracil and cytosine, 6-aza uracil, cytosine and thymine, 5-uracil (pseudouracil), 4-thiouracil, 8-halo, amino, thio, thioalkyl, hydroxyl and other 8-substituted adenines and guanines, 5-trifluoromethyl and other 5-substituted uracils and cytosines, and 7-methylguanine. Further purines and pyrimidines include those disclosed in the *Concise Encyclopedia of Polymer Science and Engineering*, J. I. Kroschwitz (ed.), John Wiley & Sons, p. 858 (1990), and those disclosed by Englisch et al, *Angewandte Chemie, International Edition*, 1991, 30, 613.

In one embodiment, functionalized nucleomonomers and oligonucleotide analogs of the invention can have a 3' and or 5' phosphorus containing moieties. Functionalized nucleomonomers can be prepared as intermediates to oligomer synthesis such as a phosphoramidite or an H-phosphonate as is well known in the art. The oligonucleotide analogs of the invention are preferably prepared by covalently linking nucleomonomers and functionalized nucleomonomers using phosphate linkages. This permits coupling via either solution phase or solid phase chemistries. Representative solution phase techniques are described in U.S. Pat. No. 5,210, 264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.) A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods. This allows for synthesis of the preferred phosphodiester or phosphorothioate phosphate linkages depending upon oxidation conditions selected. Other phosphate linkages can also be generated. These include, for example, phosphorodithioates, phosphotriesters, alkyl phosphonates, phosphoroselenates and phosphoramidates.

In another embodiment of the invention, appendage groups can be attached to functionalized nucleomonomers to enhance properties such as solubility or uptake either as a monomeric compound or to effect an oligonucleotide analog comprising one of these modified monomers. Such appendage groups are well known in the art and include, for example, selected phosphorus moieties. Phosphorous moieties amenable to the present invention include phosphates and phosphonates. Phosphate moieties include multiple phosphates linked together such as triphosphate and thiotriphosphates as disclosed in: Ludwig et al., *J. Org. Chem.,* 1989, 54, 631–635, and Tu et al., *Gene.,* 1980, 10, 177–183.

The oligomeric compounds of the present invention contain a 2'-O-alkoxyalkyl (e.g. 2'-O-methoxyethyl) modifications at the 2'-position of at least one nucleoside. This modification has been shown to increase the nuclease resistance of the oligonucleotide as well as increase the binding affinity of the oligonucleotide for its target nucleic acid strand (see Freier et al., *Nucleic Acids Research*, 1997, 25, 4429–4443). Oligomeric compounds in accordance with the present invention typically comprise from about 5 to about 50 monomeric sub-units comprising nucleomonomers and at least one functionalized nucleomonomer. It is more preferred that the oligomeric compounds of the present invention comprise from about 15 to about 25 sub-units.

Oligomeric compounds in accordance with this invention may be conveniently and routinely prepared through the well-known technique of solid-phase synthesis (Martin, *Helv. Chim. Acta,* 1995, 78, 486). Equipment for such synthesis is sold by several vendors, including Applied Biosystems (Foster City, Calif.). Any other means for such synthesis may also be employed. The actual synthesis of the oligomeric compounds of the invention is well within the talents of the art-skilled. Similar techniques may also be used to prepare oligomeric compounds having phosphorothioate linkages. It is also well-known to use similar techniques and commercially available modified amidites and controlled-pore glass (CPG) products such as biotin, fluoroscein, acridine or psoralen-modified amidites and/or CPG (Glen Research, Sterling, Va.) to synthesize fluorescently-labeled, biotinylated or other conjugated oligonucleotides. Oligomeric compounds of the present invention can also be routinely prepared by solution phase techniques that are well known and documented in the art utilizing functionalized nucleomonomers and nucleomonomers.

Oligomeric compounds of the present invention can be utilized as therapeutics, diagnostics and as research reagents and kits. They can be utilized in pharmaceutical compositions by adding an effective amount of an oligonucleotide of the invention to a suitable pharmaceutically acceptable diluent or carrier. The compounds of the invention can further be used for treating organisms having a disease characterized by the undesired production of a protein. The organism can be contacted with an oligomeric compound of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligonucleotide or an oligonucleotide analog such as an oligomeric compound in accordance with this invention, commonly in a pharmaceutically acceptable carrier, in doses ranging from 0.01 µg to 100 g per kg of body weight depending on the age of the patient and the severity of the disease state being treated. Further, the treatment regimen may last for a period of time which will vary depending upon the nature of the particular disease, its severity, and the overall condition of the patient, and may extend from once daily to once every 20 years. Following treatment, the patient is monitored for changes in bodily condition and for alleviation of the symptoms of the disease state. The dosage of the oligonucleotide may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomeric compound of the invention in conjunction with other traditional therapeutic modalities. For example, a patient being treated for AIDS may be administered an oligonucleotide in conjunction with AZT, or a patient with atherosclerosis may be treated with an oligomeric compound of the invention following angioplasty to prevent reocclusion of the treated arteries.

Following successful treatment, it may be desirable to have the patient undergo maintenance therapy to prevent the recurrence of the disease state, wherein the oligomeric compound is administered in maintenance doses, ranging from 0.01 µg to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, intranasal, transdermal, vaginal, and rectal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, powders, aqueous or oily bases, thickeners and the like may be necessary or desirable. Coated condoms, gloves and the like may also be useful.

Compositions for oral administration include powders or granules, suspensions or solutions in aqueous or nonaqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomeric compounds, and can generally be estimated based on the $EC_{50}$ found to be effective in in vitro and in vivo animal models. In general, dosage is from 0.01 $\mu$g to 100 g per kg of body weight, and may be given once or more daily, weekly, monthly or yearly, or even every 2 to 20 years.

Such therapeutic treatment can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular machinery is susceptible to such therapeutic and/or prophylactic treatment. Seemingly diverse organisms such as bacteria, protozoa, algae, plant and other higher animal forms, including warm-blooded animals, can be treated in this manner. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles (such as mitochondria and chloroplasts) of eukaryotic cells also include transcription and translation mechanisms. As such, single cells, cellular populations or organelles can be included within the definition of organisms that are capable of being treated with the therapeutic or diagnostic oligomeric compounds of the present invention. As used herein, therapeutics is meant to include eradication of a disease state, killing of an organism (such as bacteria or protozoa), or control of aberrant or undesirable cellular growth or expression.

In the context of this invention, "hybridization" refers to hydrogen bonding, which may be Watson-Creek, Hoogsteen or reversed Hoogsteen hydrogen bonding, between complementary heterocyclic bases (nucleobases). For example, adenine and thymine are complementary bases which pair through the formation of hydrogen bonds. "Complementary" as used herein refers to sequence complementarity between two nucleic acids containing nucleomonomers, one nucleic acid being an oligonucleotide and the other nucleic acid being a target DNA or RNA molecule. For example, if a nucleobase at a certain position of an oligonucleotide is capable of hydrogen bonding with a nucleobase at the same position of a DNA or RNA molecule, then the oligonucleotide and the DNA or RNA molecule are specifically hybridizable and considered to be complementary to each other at that position. The oligonucleotide and the DNA or RNA molecule are complementary to each other when a sufficient number of corresponding positions in each molecule are occupied by nucleobases which can hydrogen bond with each other. Thus, "complementary" is a term used to indicate a sufficient degree of complementarity such that stable and specific binding occurs between the oligonucleotide and the target DNA or RNA molecule. It is understood that an oligonucleotide need not be 100% complementary to its target DNA or RNA sequence to be specifically hybridizable. An oligonucleotide is specifically hybridizable when binding of the oligonucleotide to the target DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

Additional objects, advantages and novel features of this invention will become apparent to those skilled in the art upon examination of the following examples, which are not intended to be limiting.

EXAMPLE 1

General procedures for oligonucleotide synthesis

Unsubstituted and substituted oligonucleotides were synthesized on an automated DNA synthesizer (Applied Biosystems Model 380B) using standard phosphoramidite chemistry with oxidation by iodine. For phosphorothioate oligonucleotides, the standard oxidation bottle was replaced with a 0.2 M solution of 3H-1,2-benzodithiole-3-one-1,1-dioxide in acetonitrile for the step-wise thiation of the phosphite linkages. The thiation wait step was increased to 68 seconds and was followed by the capping step. After cleavage from the CPG column and deblocking using concentrated ammonium hydroxide at 55° C. for 18 hours, the oligonucleotides were purified by precipitating twice with 2.5 volumes of ethanol from a 0.5 M solution of NaCl. Analytical gel electrophoresis was accomplished in 20% acrylamide, 8 M urea, 454 mM Tris-borate buffer, pH 7. Oligonucleotides and phosphorothioates were judged, based on polyacrylamide gel electrophoresis, to be greater than 80% full-length material.

EXAMPLE 2

4-Chloro-5-iodo-2-pivaloylamino-pyrrolo[2,3-d]pyrimidine (I)

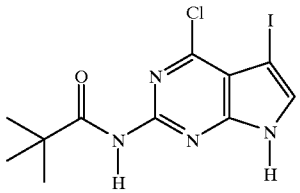

A solution of 2-amino-4-chloro-pyrrolo[2,3-d]pyrimidine (20 g, 118 mmol) and pivaloyl chloride (14.3 g, 118 mmol) in pyridine (150 mL) was stirred for 18 hours at ambient temperature. The resulting dark red solution was evaporated to an amber solid which was co-evaporated with water (20 mL, 3x). The resulting solid was filtered, washed with cold water and then dried over KOH in vacuo to yield 22 g (83%) of 2-pivaloylamino-4-chloro-pyrrolo[2,3-d]pyrimidine as a reddish solid. $^1$H-NMR (DMSO-$d_6$): δ 12.35 (bs, 1, N (7)-H); 10.07 (s,1, N (2)-H); 7.56 (m,1, H-6); 6.58 (m,1, H-5); 1.24 (s, 9, pivaloyl methyls). mp>210° C.

A solution of the 2-pivaloylamino-4-chloro-pyrrolo[2,3-d]pyrimidine (21.5 g, 85 mmol) and N-iodosuccinimide (19.12 g, 85 mmol) in DMF (150 mL) was stirred at ambient temperature for 18 hr. The red solution was evaporated to an amber residue which upon trituration with cold water gave a yellow solid. The solid was collected by filtration, the filter cake was washed with cold water and then dried in vacuo to yield 30.5 g (94%) of the title compound. $^1$H-NMR (DMSO-$d_6$): δ 12.72 (s,1, N (7)-H); 10.14 (s,1, N(2)-H); 7.78 (d,1, H-6); 1.24 (s, 9, pivaloyl methyls). mp 218–220° C.

EXAMPLE 3

1-Chloro-5-(t-butyldimethylsilyloxy)-2,3-isopropylidene ribose (II)

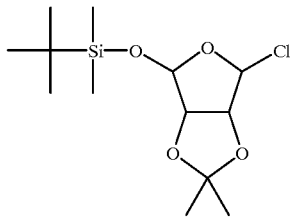

To a dry 50 mL round bottom flask was added 1 g (3.3 mmoles) of 5-O-(t-butyldimethylsilyl)-2,3-O-isopropylidene ribose, 0.7 g (4.4 mmoles) carbon tetrachloride and 5 mL of tetrahydrofuran. The reaction mixture was cooled to −10° C. in a methanol/ice bath and then 0.62 mL (3.3 mmoles) of HMPT added dropwise over a period of 3 minutes. The solution was then stirred at −10° C. for 5 minutes and used directly for the synthesis of 4-chloro-7-iodo-2-pivaloylamino-7-deazapurin-9-yl-2',3'-O-isopropylidene-5'-O-t-butyldimethylsilyl riboside (III).

EXAMPLE 4

4-Chloro-7-iodo-2-pivaloylamino-7-deazapurin-9-yl-2',3'-isopropylidene-5'-t-butyldimethylsilyl riboside (III)

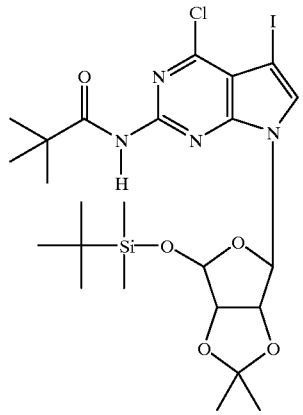

A dry 100 mL round bottom flask was charged with 0.6 g. (1.6 mmoles) of 4-chloro-7-iodo-2-pivaloylamino-7-deazapurine (I) and 20 mL of dry acetonitrile. To this was added 100 mg (2.4 mmoles) of 60% sodium hydride in mineral oil. Evolution of hydrogen was observed and the reaction mixture stirred for 30 minutes following the cessation of hydrogen evolution. The freshly prepared 1-chloro-5-O-(t-butyldimethylsilyloxy)-2,3-O-isopropylidene-ribose (II) was then directly added to the reaction mixture over a period of 10 minutes. The reaction was then stirred at room temperature overnight and progress of the reaction monitored by tlc (silica gel; 1:1 hexanes/ethyl acetate). When the reaction was observed to have proceeded to completion (all starting heterocycle (I) had been consumed) the suspension was filtered through celite and the filtrate concentrated on a rotary evaporator. The crude product so obtained was purified by silica gel column chromatography using 3:1 hexanes/ethyl acetate as the eluant. The fractions containing the β-nucleoside product, as observed by tlc, were pooled and concentrated to give a 38.5% of the title compound.

EXAMPLE 5

4-Chloro-7-iodo-2-pivaloylamino-7-deazapurin-9-yl riboside (IV)

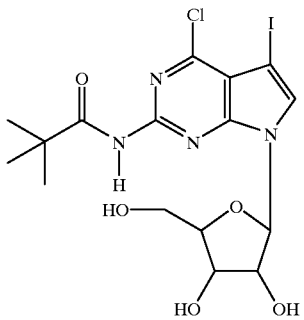

To a solution of the protected nucleoside (III) in DMF is added formic acid with stirring at room temperature overnight. The solution is concentrated on a rotary evaporator and the residue is treated with dry tetrahydrofuran. To this is added a solution of tetrabutylammonium fluoride in tetrahydrofuran and the reaction allowed to stir at room temperature for several hours. The reaction is monitored for disappearance of the silyl-protected nucleoside by tlc and upon completion of the reaction the solution is treated with equal amounts of water and methylene chloride. The phases are separated, and the organic phase is washed several times with equal volumes of water and then dried with magnesium sulfate. The mixture is filtered and the solution concentrated on a rotary evaporator to afford the crude deprotected nucleoside product. The crude material is purified by silica gel flash column chromatography to give the title compound.

EXAMPLE 6

4-Chloro-7-iodo-2-pivaloylamino-7-deazapurin-9-yl-4',5'-O-(dichlorobenzyl) riboside (V)

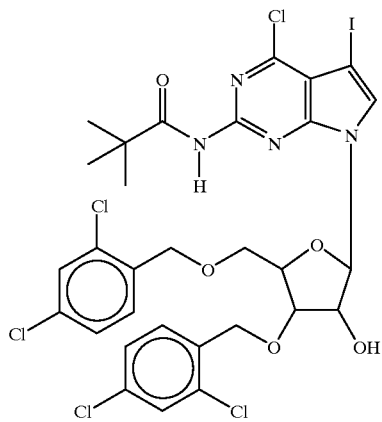

V

To a solution of 4-chloro-7-iodo-2-pivaloylamino-7-deazapurin-9-yl riboside (IV) dissolved in dry DMF is added a suspension of sodium hydride in mineral oil. The mixture is stirred at room temperature for 30 minutes following the cessation of hydrogen evolution. To this mixture is added a solution of dichlorobenzyl chloride in DMF over a period of 15 minutes. The mixture is stirred at room temperature for several hours and monitored by tlc. Upon completion of the reaction as seen via tlc, the reaction mixture is cooled to 0° C. in an ice bath and a solution of tin tetrachloride in dry methylene chloride added. Following reaction for several hours, the reaction mixture is concentrated in vacuo and the residual solution treated with excess methylene chloride and water. The phases are separated and the organic phase washed with sodium bicarbonate and water, dried (magnesium sulfate) and concentrated to afford the crude product. The crude material is purified by silica gel flash column chromatography to give the title compound.

EXAMPLE 7

4-Chloro-7-iodo-2-pivaloylamino-7-deazapurin-9-yl-2'-O-(methoxyethyl)-4',5'-O-(dichlorobenzyl) riboside (VI)

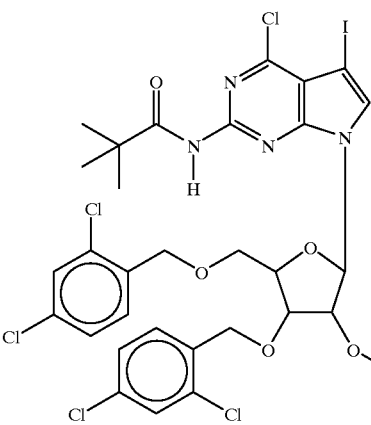

VI

The 4-chloro-7-iodo-2-pivaloylamino-7-deazapurin-9-yl-4',5'-O-(dichlorobenzyl) riboside (V) is placed in a dry round bottom flask and dissolved in dry tetrahydrofuran. To this solution is added, under argon, a suspension of sodium hydride in mineral oil and the mixture stirred at room temperature for 1 hour. To this is then added a solution of 2-methoxy-chloroethane in dry THF over a period of 30 minutes and the reaction mixture is stirred at room temperature for several additional hours. When tlc monitoring indicated the reaction to have consumed all starting nucleoside (V), the reaction mixture is filtered through celite and the filtrate concentrated in vacuo. The crude material is purified by silica gel flash column chromatography to give the title compound.

EXAMPLE 8

2,4-Diamino-7-iodo-7-deazapurin-9-yl-2'-O-(methoxyethyl)-4',5'-O-(dichlorobenzyloxy) riboside (VII)

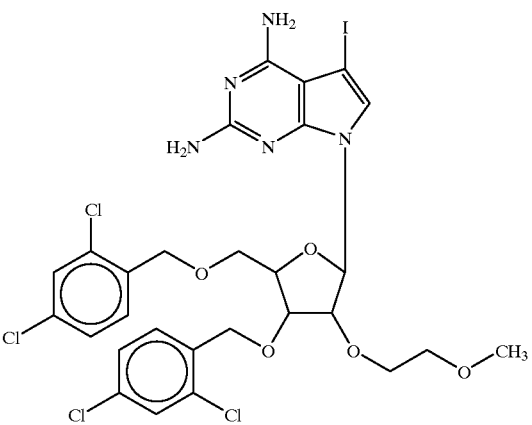

VII 4-chloro-7-iodo-2-pivaloylamino-7-deazapurin-9-yl-2'-(methoxyethyl)-4',5'-O-(dichlorobenzyloxy) riboside (VI) is dissolved into a saturated solution of ammonia in methanol and this solution heated at 100° C. for several hours in a tightly sealed reaction vessel. The reaction is cooled to <10° C., opened and the solution concentrated on a rotary evaporator to afford the 2-amino nucleoside. The crude material is purified by silica gel flash column chromatography to give the title compound.

EXAMPLE 9

2,4-Di(benzoylamino)-7-iodo-7-deazapurin-9-yl-2'-(methoxyethyl)-riboside (VIII)

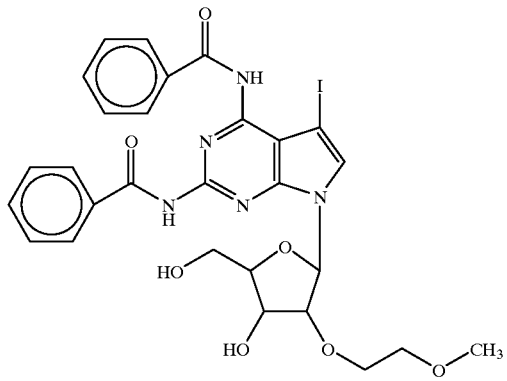

VIII

Step A

A solution of 2,4-diamino-7-iodo-7-deazapurin-9-yl-2'-(methoxyethyl)-4',5'-O-(dichlorobenzyl) riboside (VII) in ethanol is treated with hydrogen at room temperature under pressure for several hours. When hydrogenolysis of the dichlorobenzyl protecting groups is complete, as observed by tlc, the reaction mixture is concentrated in vacuo and the crude 2,4-diamino-7-iodo-7-deazapurin-9-yl-2'-O-(methoxyethyl)-riboside is used directly in Step B.

Step B

The 2,4-diamino-7-iodo-7-deazapurin-9-yl-2'-O-(methoxyethyl)-riboside (obtained either from Step A above or from the Example 14 below (compound XII) is benzoylated using slightly more than two equivalents of benzoyl chloride in pyridine at room temperature. The reaction is allowed to proceed overnight until complete as indicated by tlc and concentrated. The crude concentrate is purified by silica gel flash column chromatography to give the title compound.

EXAMPLE 10

2,4-Di(benzoylamino)-7-iodo-7-deazapurin-9-yl-2'-(methoxyethoxy)-5'-O-DMT-riboside-3'-cyanoethyl phosphoramidite (IX)

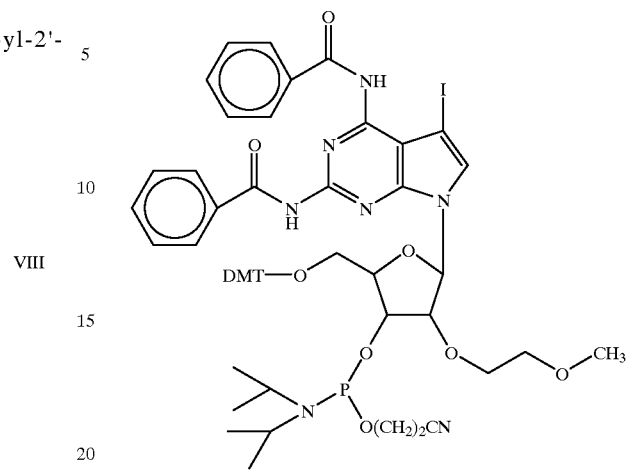

IX

Tritylation

A solution of the nucleoside (VIII) in pyridine is treated with excess dimethoxytrityl chloride and the reaction mixture stirred overnight at room temperature. The solution is concentrated and the resulting residue is purified by silica gel flash column chromatography. The purified tritylated material is used directly for phosphitylation.

Phosphitylation

The 5'-O-DMT nucleoside is dried by co-evaporation with dry pyridine, toluene and finally tetrahydrofuran. This material (3 mmoles) is dissolved in dry THF (20 mL) and 12 mmoles of diisopropylethyl amine. To this solution is added a solution of 6 mmoles chloro-(2-cyanoethoxy)-N,N,-diisopropylaminophosphine, under argon, over a period of 5 minutes. The reaction mixture is stirred for an additional 60 minutes and then filtered. The filtrate is concentrated in vacuo and the residue dissolved in ethyl acetate. The solution is washed twice with ice-cold sodium bicarbonate solution, dried with magnesium sulfate, filtered and concentrated on a rotary evaporator. The residue is dissolved into ethyl acetate and this solution added, dropwise, to vigorously stirred hexane at −78° C. The resulting suspension is rapidly filtered and the precipitate dried under vacuum to afford the phosphoramidite product (IX).

EXAMPLES 11–15

Alternate route for the preparation of Compound IX

Example 11

4-Chloro-7-iodo-2-pivaloylamino-7-deazapurin-9-yl-2',3',5'-tri-O-(benzoyl) riboside (X)

To a solution of 4-chloro-7-iodo-2-pivaloylamino-7-deazapurine (I) in dry tetrahydrofuran is added bis(trimethylsilyl)acetamide and trimethylsilyl triflate and the mixture allowed to stir under argon for 30 minutes. To this mixture a solution of 2,3,5-tribenzoyloxy-ribose-1-acetate in dry tetrahydrofuran is added dropwise over a period of 15 minutes. The reaction is allowed to proceed under an inert atmosphere at room temperature for several hours. Upon completion of reaction as indicated by tlc the reaction mixture is concentrated and the residue treated with equal volumes of methylene chloride and water. The organic phase is washed with water, dried with magnesium sulfate and concentrated to afford the crude nucleoside product. The crude nucleoside product is purified by silica gel flash column chromatography to give the title compound.

Example 12
4-Chloro-7-iodo-2-pivaloylamino-7-deazapurin-9-yl-3',5'-di-O-(benzoyl) riboside (XI)

Selective hydrolysis of the 2'-O-benzoyl groups is accomplished via treatment of 4-chloro-7-iodo-2-pivaloylamino-7-deazapurin-9-yl-2',3',5'-tri-O-(benzoyl) riboside (X) with a solution of hydrazine in acetic acid. The reaction mixture is stirred for several hours, concentrated and the residue purified by silica gel flash column chromatography to give the title compound.

Example 13
4-Chloro-7-iodo-2-pivaloylamino-7-deazapurin-9-yl-2'-O-(methoxyethyl)-3',5'-di-O-(benzoyl) riboside (XII)

4-Chloro-7-iodo-2-pivaloylamino-7-deazapurin-9-yl-3',5'-di-O-(benzoyloxy) riboside (XI) is placed in a dry round bottom flask and dissolved in dry tetrahydrofuran. To this solution is then added, under argon, a suspension of sodium hydride in mineral oil and the mixture stirred at room temperature for 1 hour. To this is added a solution of 2-methoxychloroethane in dry THF over a period of 30 minutes and the reaction mixture is stirred at room temperature for several additional hours. Upon completion of reaction as indicated by tlc, the reaction mixture is filtered through celite and the filtrate concentrated in vacuo. The concentrate is purified by silica gel flash column chromatography to give the title compound.

Example 14
Synthesis of 2,4-diamino-7-iodo -7-deazapurin-9-yl-2'-O-(methoxyethyl)-riboside (XIII)

4-Chloro-7-iodo-2-pivaloylamino-7-deazapurin-9-yl-2'-O-(methoxyethyl)-3',5'-di-O-(benzoyl) riboside (XII) is dissolved into a saturated solution of ammonia in methanol. The resulting solution is heated at 100° C. for several hours in a tightly sealed reaction vessel. The reaction is cooled to <10° C., opened and the solution concentrated on a rotary evaporator to a residue. The residue is purified by silica gel flash column chromatography to give the title compound.

Example 15
2,4-Di(benzoylamino)-7-iodo-7-deazapurin-9-yl-2'-O-(methoxyethyl)-5'-O-DMT-riboside-3'-O-cyanoethyl phosphoramidite (IX)

2,4-Diamino-7-iodo -7-deazapurin-9-yl-2'-O-(methoxyethyl)-riboside (XIII) is treated as per the procedures illustrated in Example 9, Step B, to benzoylate the 2,4-exocyclic amino groups. The crude material is purified and the purified material is treated as per the procedures illustrated in Example 10 to give the protected phosphoramidite, compound IX, by a second route (Examples 11–15).

EXAMPLE 16
2-amino-5-bromo-2,3-dicyanopyrrole

A solution of tetracyanoethylene (14.5 g, 113 mmol) in acetone (81 mL) and ethyl acetate (171 mL) was treated with a solution of HBr in acetic acid (33%, 81 mL) while maintaining the internal temperature at 0–5° C. The reaction mixture was stirred for an additional 30 minutes and the resulting yellow solid was filtered, washed with cold water and air dried. The solid was suspended in water (150 mL). The pH of the suspension was adjusted to 11 with NaOH (50%/H$_2$O) to achieve a solution and stirred for 15 minutes. The solution was treated with glacial acetic acid to pH 5 to yield a precipitate. The precipitate was filtered and dried over KOH in vacuo to give 18.6 g (78%) of the title compound. $^1$H-NMR (DMSO-d$_6$): δ 12.3 (br s, 1, N—H); 6.46 (br s, 2, NH$_2$). mp >210° C.

What is claimed is:

1. A functionalized nucleomonomer of the formula:

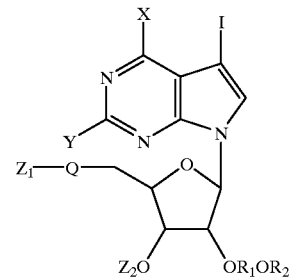

wherein:

X is Cl, OH, SH, SR$_3$, OR$_1$, CN or N(H)J;

Y is OH, SH, SR$_3$, OR$_3$, CN or N(H)J;

each J is, independently, hydrogen or an amino protecting group;

Q is O or CH$_2$;

Z$_1$ is H, a group useful in oligonucleotide synthesis or a phosphorus containing moiety;

Z$_2$ is H, a phosphorus containing moiety, or a group useful in oligonucleotide synthesis; and each R$_1$, R$_2$ and R$_3$ is, independently, C$_1$–C$_{10}$ alkyl.

2. The functionalized nucleomonomer of claim 1 wherein said phosphate moiety is selected from the group consisting of —P(OR$_3$)NR$_4$R$_5$, P(=O)(OR$_6$)$_2$, —P(OR$_7$)H, —PO$_3$$^{-2}$, —PO$_2$H$^-$, P(=S)O$_2$$^{-2}$ and P(=O)(OR$_8$)O—;

each R$_4$ and R$_5$ is, independently, straight or branched chain C$_1$–C$_{10}$ alkyl, or R$_4$ and R$_5$ together are —(CH$_2$)$_n$— or —(CH$_2$)$_n$—O—(CH$_2$)$_n$;

each R$_6$ is, independently, H, C$_1$–C$_{10}$ alkyl, aryl or haloaryl;

R$_7$ is selected from a group consisting of H, C$_1$–C$_{10}$ alkyl, aryl and haloaryl;

R$_8$ is haloaryl; and n is 2 to 7.

3. The functionalized nucleomonomer of claim 1 wherein R$_1$ is —CH$_2$—CH$_2$— and R$_2$ is —CH$_3$.

4. The functionalized nucleomonomer of claim 1 wherein X is NH$_2$, Y is NH$_2$, R$_1$ is —CH$_2$—CH$_2$— and R$_2$ is —CH$_3$.

5. The functionalized nucleomonomer of claim 1 wherein X is OH, Y is NH$_2$, R$_1$ is —CH$_2$—CH$_2$— and R$_2$ is —CH$_3$.

6. The functionalized nucleomonomer of claim 1 wherein said group useful in oligonucleotide synthesis is trityl, methoxytrityl or dimethoxytrityl.

7. An oligonucleotide analog comprising a sequence of covalently bound nucleomonomers wherein at least one of said nucleomonomers is a functionalized nucleomonomer of the formula:

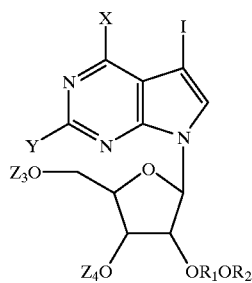

wherein:

X is Cl, OH, SH, $SR_3$, $OR_1$, CN or N(H)J;

Y is OH, SH, $SR_3$, $OR_3$, CN or N(H)J;

each J is, independently, H or an amine protecting group;

each $Z_3$ and $Z_4$ is, independently, H or an internucleoside linkage with the proviso that only one of $Z_3$ and $Z_4$ can be H; and each $R_1$, $R_2$ and $R_3$ is, independently, $C_1$–$C_{10}$ alkyl.

8. The oligonucleotide of claim 7 wherein $R_1$ is —$CH_2$—$CH_2$— and $R_2$ is —$CH_3$.

9. The oligonucleotide of claim 7 wherein X is $NH_2$, Y is $NH_2$, $R_1$ is —$CH_2$—$CH_2$— and $R_2$ is —$CH_3$.

10. The oligonucleotide of claim 7 wherein X is OH, Y is $NH_2$, $R_1$ is —$CH_2$—$CH_2$— and $R_2$ is —$CH_3$.

11. The oligonucleotide analog of claim 7 wherein said phosphate moiety is selected from the group consisting of —P($OR_3$)$NR_4R_5$, P(=O)($OR_6$)$_2$, —P($OR_7$)H, —$PO_3^{-2}$, $PO_2H^-$, P(=S)$O_2^{-2}$ and P(=O)($OR_8$)O—;

wherein each $R_4$ and $R_5$ is, independently, straight or branched chain $C_1$–$C_{10}$ alkyl, or $R_4$ and $R_5$ together are —$(CH_2)_n$— or —$(CH_2)_n$—O—$(CH_2)_n$;

each $R_6$ is, independently, H, $C_1$–$C_{10}$ alkyl, aryl or haloaryl;

$R_7$ is selected from the group consisting of H, $C_1$–$C_{10}$ alkyl, aryl and haloaryl;

$R_8$ is haloaryl; and n is 2 to 7.

* * * * *